United States Patent [19]

Cohen et al.

[11] Patent Number: 5,011,628
[45] Date of Patent: Apr. 30, 1991

[54] N,N'-DIARYLBENZAMIDINES USEFUL AS ULTRAVIOLET LIGHT ABSORBERS

[75] Inventors: Isaac D. Cohen, Brooklyn, N.Y.; Joseph A. Virgilio, Wayne, N.J.

[73] Assignee: Givaudan Corporation, Clifton, N.J.

[21] Appl. No.: 336,286

[22] Filed: Apr. 11, 1989

Related U.S. Application Data

[63] Continuation-in-part of Ser. No. 207,088, Jun. 15, 1988, abandoned.

[51] Int. Cl.$^5$ ............... F21V 9/04; C07C 257/00; C07C 229/00; C07C 255/00
[52] U.S. Cl. ............................. 252/589; 560/35; 558/422; 562/440; 564/157; 564/166; 564/167; 564/245; 564/247
[58] Field of Search ............... 252/588, 589, 587, 582; 560/35; 562/440; 558/422; 564/157, 166, 167, 245, 247

[56] References Cited

U.S. PATENT DOCUMENTS

| | | | |
|---|---|---|---|
| 4,021,471 | 5/1977 | Virgilio et al. | 252/589 |
| 4,085,062 | 5/1978 | Virgilio et al. | 252/589 |

FOREIGN PATENT DOCUMENTS

| | | | |
|---|---|---|---|
| 5088046 | 7/1975 | Japan | 564/245 |
| 1114674 | 9/1984 | U.S.S.R. | 564/245 |
| 1267009 | 3/1972 | United Kingdom . | |

OTHER PUBLICATIONS

Y. Mori and J. Tsuji, Tetrahedron 27 (1971), pp. 3811-3819.
J. Sevcik, Acta. Univ. Palacki Olomuc., Fac. Reurm Nat., 1976, 49 (Chem 15), pp. 47-51.
Chemical Abstracts 87: 38331t (1977).
A. C. Hontz and E. C. Wagner, Org. Syn., Coll. vol. IV, John Wiley & Sons, New York, 1963, pp. 383-386.
S. P. Joshi et al., J. Chem. Soc., (1936), pp. 793-797.
J. A. Smith and H. Taylor, J. Chem. Soc.(B), 1969, 64-65.
J. Sevcik, Monatshefte fur Chemie, 100, 1307-1309 (1969).
Chem. Abstract 81:91185a [for J. Sevcik, Acta Univ. Palacki, Olomuc., Fac. Rerum Natur. 1973, 41, Chemica 13, 131-138.]
Chem. Abstract 90:129436j [for J. Sevcik, Acta Univ. Palacki, Olomuc., Fac. Rerum Natur. 1977, 53 (Chem. 16)37-46.]

*Primary Examiner*—John S. Maples
*Assistant Examiner*—Philip Tucker
*Attorney, Agent, or Firm*—Robert F. Tavares; Linda A. Vag

[57] ABSTRACT

Substituted benzamidines and their hydrochloride salts are useful as ultraviolet light absorbers, the benzamidines having the formula

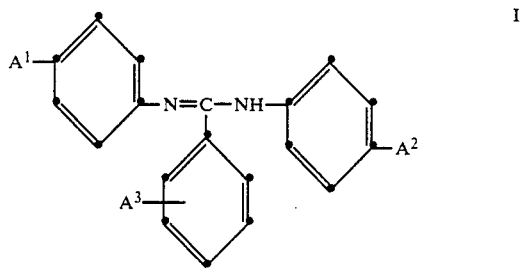

wherein:
A$^1$ and A$^2$ may be the same or different and represent —COOR$^1$, —CONR$^1$R$^2$, —C≡N or —C$_6$H$_5$;
A$^3$ represents —H, —OH, —OR, —Cl, —NO$_2$, —C≡N, —C$_6$H$_5$, or an alkyl group of one to five carbon atoms;
R$^1$ and R$^2$ may be the same or different and represent hydrogen or an alkyl group of one to ten carbon atoms; and,
R represents an alkyl group of one to ten carbon atoms.

20 Claims, No Drawings

N,N'-DIARYLBENZAMIDINES USEFUL AS ULTRAVIOLET LIGHT ABSORBERS

This application is a continuation-in-part of application Ser. No. 07/207,088 filed Jun. 15, 1988, now abandoned.

BACKGROUND OF THE INVENTION

1. Field of the Invention

This invention discloses novel ultraviolet absorbing N,N'-diarylbenzamidines useful for protecting materials against the degradative effects of ultraviolet light.

2. Background Art

Various polymers, plastics, resins, cosmetics, dyes, pigments, lacquers, varnishes, textiles, etc., which are subject to photodegradation by UV-radiation, can be protected by incorporating therein suitable UV-light absorbing agents which will absorb the harmful rays and convert them to relatively harmless forms of energy. To be effective, the light absorbing agent must absorb light efficiently in the ultraviolet portion of the sun's rays which reach the earth, i.e., the range of 280 to 400 nanometers. The agent should also be stable to UV-radiation, compatible with and stable in the medium in which it is incorporated, possess little or no color, be non-toxic, thermally stable, and have low volatility.

The prior art does not teach the novel N,N'-diarylbenzamidines, which are disclosed herein, to be valuable UV-light absorbing agents.

SUMMARY OF THE INVENTION

In accordance with the present invention, there are provided N,N'-diarylbenzamidines of the formula

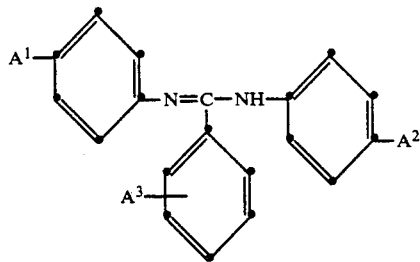

wherein:

$A^1$ and $A^2$ may be the same or different and are selected from the group consisting of acids, esters, amides, nitriles and aryl radicals, and, $A^3$ is selected from the group consisting of hydrogen, nitrile, nitro, halogen, ethers, acids, esters, amides, aryl radicals and alkyl radicals.

The benzamidines of this invention are particularly valuable inasmuch as they absorb radiation in both the UV-A and UV-B regions and are particularly effective in the range of 280 to 375 nanometers. They are stable to photodegradation and thermal degradation. They are colorless or nearly colorless at the concentrations used, which makes them particularly valuable in retarding photodegradation in those cases where color could be a problem, such as in clear plastics. They are resistant to attack by polar solvents, such as methanol, ethanol, isopropanol, and the like, which makes them particularly valuable in applications based on alcoholic and hydroalcoholic solutions, suspensions, emulsions and the like.

DESCRIPTION OF THE PREFERRED EMBODIMENTS

As indicated above, the novel benzamidines of this invention have the formula

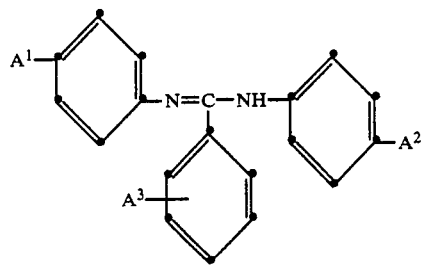

wherein:

$A^1$ and $A^2$ may be the same or different and are selected from the group consisting of acids, esters, amides, nitriles and aryl radicals, and, $A^3$ is selected from the group consisting of hydrogen, nitrile, nitro, halogen, ethers, acids, esters, amides, aryl radicals and alkyl radicals.

While $A^1$ and $A^2$ can be any suitable electron withdrawing group, those compounds wherein $A^1$ and $A^2$ are acids, esters, amides, nitriles or aryl radicals are the more readily available. Preferred are compounds wherein $A^1$ and $A^2$ are selected from the group consisting of —$COOR^1$, —$CONR^1R^2$, —C≡N and —$C_6H_5$. The nature of $R^1$ and $R^2$ has very little influence on the UV-absorbing properties of the benzamidine I and may be hydrogen or any suitable alkyl, aryl or aralkyl group. The more readily available esters and amides wherein $R^1$ or $R^2$ is a lower alkyl group of from one to ten carbon atoms are preferred with methyl and ethyl being especially preferred. The most preferred compounds are those wherein $A^1$ and $A^2$ are methyl or ethyl ester groups.

While $A^1$ and $A^2$ may be the same or different, it is preferred to have $A^1$ and $A^2$ be the same for simplicity and economy of synthesis.

The nature of $A^3$ does not appear to have a large influence on the UV-absorbing properties and may be any suitable group, e.g. hydrogen, a nitrile, a halogen, a nitro group, an ether, an acid, an ester, an amide, an aryl radical, an alkyl radical or the like. The more readily available starting materials are those wherein $A^3$ is selected from the group consisting of —H, —OH, —$NO_2$, —Cl, —C≡N, —$C_6H_5$, alkyl groups of one to five carbon atoms and ether radicals of the type —OR wherein R is an alkyl group of from one to ten carbon atoms. Especially preferred are those benzamidines wherein $A^3$ is chosen from the group consisting of hydrogen and methoxy.

A number of methods known in the art can be adapted to prepare the novel N,N'-diarylbenzamidines of the present invention. [See, for example, A. C. Hontz, E. C. Wagner, Org. Syn., Coll. Vol. IV, John Wiley & Sons, Inc., New York, 383 (1963); S. P. Joshi, A. P. Khanolkar, T. S. Wheeler, J. Chem. Soc., 793 (1936)]. Scheme I below sets forth a convenient method for preparing those compounds of formula I wherein $A^2$ is identical to $A^1$.

Scheme I

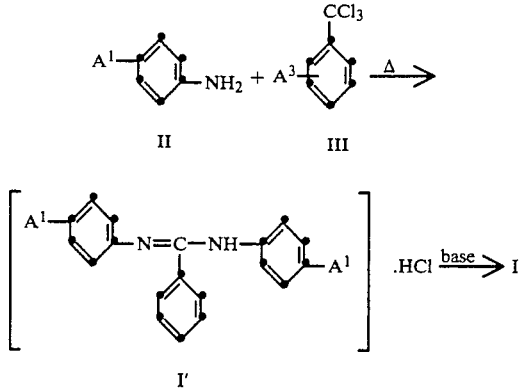

In this process, it is preferred to react about two moles of the appropriate substituted aniline, II, with each mole of the appropriate substituted benzotrichloride, III, used. In the preferred process of this invention the reactants II and III, above, are heated to reflux in an aromatic solvent such as toluene or xylene for about twelve to twenty-four hours. The reaction mixture is then cooled to about 0° C. The hydrochloride salt I' precipitates and can be removed by simple filtration. In those instances wherein the hydrochloride salt itself is preferred as the UV-absorbing agent, it can be used as such. In most instances however, it is preferred to use the benzamidine per se and the benzamidine may be liberated by treating the hydrochloride salt with dilute base.

The use of a solvent is not essential. The reaction may be carried out in the absence of solvent. The addition of an aromatic solvent to the reaction mixture does, however, facilitate control of the exothermic condensation and is generally preferred. The use of refluxing xylene for this reaction is especially preferred.

Those compounds of formula I wherein $A^1$ is not the same as $A^2$ may be conveniently prepared, as illustrated in Scheme II.

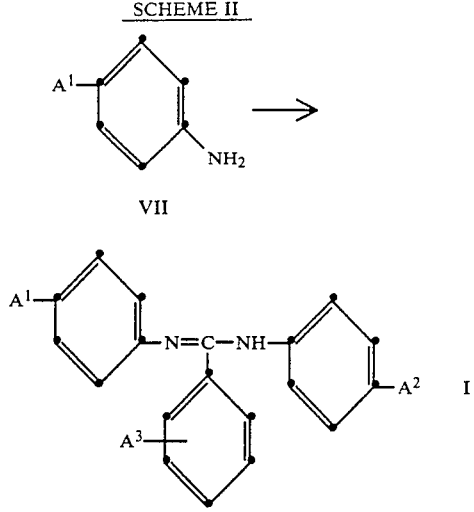

As shown in Scheme II, the appropriate aniline, V, is reacted with the appropriate benzoyl halide, IV, in approximately equimolar ratios to form the benzamide derivative, VI. This benzamide derivative, VI, is subsequently condensed with a second and different aniline, VII, in the presence of an activating agent, such as $PCl_5$, $POCl_3$, or the like, to provide the hydrochloride salt of I. The hydrochloride salt is usually converted to I during the basic workup procedure. Typical procedures are provided in the examples.

Of course, the method of Scheme II could also be used to prepare those benzamidines wherein $A^1$ and $A^2$ are identical, simply by using the same aniline for both steps, i.e., V and VII would be the same. In this case, steps 1 and 2 may be run concurrently by allowing approximately two moles of the aniline, V, to react with one mole of the benzoyl halide, IV, in the presence of the activating agent. Alternatively, the acid precursor of IV may be used, in which case the benzoyl halide is formed in situ. The methods of preparation, which are not critical to this invention, are further illustrated in the examples provided herein.

Table I lists the strong ultraviolet-absorbing properties of several benzamidines prepared by either Scheme I or Scheme II. The absorptions were determined by dissolving the compounds in isopropanol and recording the spectrum on an ultraviolet spectrophotometer. Table I lists the wavelength of maximum absorption ($\lambda$ max), the intensity of this absorption as molar extinction coefficient ($\epsilon$ max), and the $\lambda$ range where $\epsilon = 5,000$ or greater. Also, given in Table I, are the UV characteristics of two hydrochloride salts. (The benzamidines of this invention have a basic nitrogen and can be converted into their hydrohalide salts if desirable for certain applications. It is also possible to isolate the hydrochloride salt from the reaction medium since in both Scheme I and Scheme II, as discussed above, the hydrochloride salt is formed as a reaction intermediate which must be treated with base to provide the benzamidine per se.)

TABLE 1

| Entry | Scheme | Compound | λ max (nm) | ε max | λ Range* (nm) ε > 5,000 |
|---|---|---|---|---|---|
| 1 | I | N,N'-bis(4-methoxy-carbonylphenyl)benzamidine | 318 | 27,800 | 280–374 |

TABLE 1-continued

| Entry | Scheme | Compound | λ max (nm) | ε max | λ Range* (nm) ε > 5,000 |
|---|---|---|---|---|---|
| 2 | I | N,N'-bis(4-ethoxy-carbonylphenyl)benzamidine | 320 | 26,300 | 280–373 |
| 3 | I | N,N'-bis(4-[2-ethylhexyl]-oxycarbonylphenyl)benzamidine | 320 | 23,000 | 280–375 |
| 4 | I | N,N'-bis(4-n-octylcarbamyl-phenyl)benzamidine | 296 | 21,800 | 280–368 |
| 5 | II | N-(4-biphenyl)-N'-(4-ethoxy-carbonylphenyl)benzamidine | 288 | 26,400 | 280–378 |
| 6 | II | N,N'-bis(4-ethoxycarbonyl-phenyl)-2-methoxybenzamidine | 318 | 31,300 | 280–366 |
| 7 | II | N,N'-bis(4-ethoxycarbonyl-phenyl)-4-methoxybenzamidine | 322 | 26,200 | 280–370 |
| 8 | II | N,N'-bis(4-ethoxycarbonyl-phenyl)-4-cyanobenzamidine | 302 | 27,600 | 280–371 |
| 9 | II | N,N'-bis(4-ethoxycarbonyl-phenyl)-4-phenylbenzamidine | 292 | 28,800 | 280–385 |
| 10 | I | N,N'-bis(4-ethoxycarbonyl-phenyl)-2-chlorobenzamidine | 302 | 25,000 | 280–350 |
| 11 | II | N,N'-bis(4-ethoxycarbonyl-phenyl)-3-chlorobenzamidine | 300 | 24,200 | 280–368 |
| 12 | II | N,N'-bis(4-ethoxycarbonyl-phenyl)-4-chlorobenzamidine | 318 | 24,000 | 280–372 |
| 13 | II | N,N'-bis(4-ethoxycarbonyl-phenyl)-4-methylbenzamidine | 315 | 19,100 | 280–369 |
| 14 | II | N,N'-bis(4-ethoxycarbonyl-phenyl)-4-t-butylbenzamidine | 322 | 24,500 | 280–376 |
| 15 | II | N,N'-bis(4-ethoxycarbonyl-phenyl)-4-nitrobenzamidine | 304 | 36,200 | 280–378 |
| 16 | I | N,N'-bis(4-ethoxycarbonyl-phenyl)-benzamidine hydrochloride | 320 | 27,000 | 280–376 |
| 17 | II | N,N'-bis(4-ethoxycarbonyl-phenyl)-4-nitrobenzamidine hydrochloride | 302 | 32,300 | 280–367 |

*Only wavelengths above 280 nm are included.

All of the benzamidines set forth in Table I, can be characterized by their high absorptivity and the broad range over which the absorptivity is effective. High absorption over a broad range is an especially desirable property of a commercial UV-screening agent since, in practice, it is often difficult to determine the wavelength which will be most deleterious to the material to be protected. The benzamidines of Table I also show excellent resistance to photochemical and thermal degradation.

Sensitive materials can be protected from the harmful effects of UV-light by incorporating an N,N'-diarylbenzamidine of the invention into the UV-sensitive material or into materials used to coat or protect UV-sensitive materials. They can be admixed with dyes or cosmetics to preserve the integrity of these materials. Incorporation into plastics prevents discoloration, etc. which may occur in the absence of an effective UV-absorber.

UV-sensitive materials can also be protected from the harmful rays by coating with a material containing the UV-screening agent. The compositions of this invention can be incorporated into lotions to protect the skin from UV-radiation, or incorporated into plastic containers or container coatings which will serve to protect the contents of such containers from the harmful effects of UV-radiation.

The effective amounts of screening agent necessary for each application would be dependent on that application and determinable by those skilled in the art. For most applications, a preferred range of 0.01 wt percent to 4 wt percent is effective, with 0.05 wt percent to 2 wt percent being especially preferred. However, in special formulations where higher concentrations are needed, amounts as high as 8 wt percent may be used. Such high amounts are often required in cosmetic formulations.

ILLUSTRATION OF THE PREFERRED EMBODIMENTS

The following examples provide a more detailed explanation of the invention and are intended as illustrations and not limitations of the invention. For examples 1 through 5, melting points were determined in open-ended capillary tubes and are not corrected; 60 MHz, $^1$H-NMR chemical shifts are reported downfield from internal tetramethylsilane (TMS) on the δ scale; and IR absorptions are reported in reciprocal centimeters.

EXAMPLE 1

Scheme I: Preparation of N,N'-Bis(4-ethoxycarbonylphenyl)benzamidine, 2 a. N,N'-Bis(4-ethoxycarbonylphenyl)benzamidine hydrochloride, 16

To a stirred suspension of ethyl 4-aminobenzoate (165.0 g; 1.0 mole) in xylene (465 mL) was added α,α,α-trichlorotoluene (100.7 g; 0.52 mole). The mixture was allowed to reflux for 18 h, then was cooled to 0° C. and filtered. The resultant precipitate was washed with ice-cold xylene (2×70 mL), triturated with hot toluene and dried to yield the salt (89.8 g; 39.7%) as white crystals: mp 214.0°–215.5° C. $^1$H-NMR (CDCl$_3$) 8.0–6.9 (m, 14H), 4.3 (q, 4H, J=7 Hz), 1.4 (t, 6H, J=7 Hz); IR (CHCl$_3$) 1715, 1600; MS (m/e) 416 (M+−HCl), 252 (base).

b. N,N'-Bis(4-ethoxycarbonylphenyl)benzamidine, 2

The salt prepared as in part a (53.6 g), was added to a vigorously stirred mixture of ice-water (500 mL), concentrated ammonium hydroxide (20 mL), and toluene (100 mL). After filtering and drying one obtains the benzamidine (37.1 g; 75.3%) as a pale-yellow solid: mp 170°–172° C. $^1$H-NMR (CDCl$_3$) 8.0–7.0 (m, 14H), 4.2 (q, 4H, J=6 Hz), 1.3 (t, 6H, J=6 Hz); IR (CHCl$_3$) 3330, 1700, 1590; MS (m/e) 416 (m+), 105 (base).

EXAMPLE 2

Scheme II: Preparation of N,N'-Bis(4-ethoxycarbonylphenyl)-4-nitrobenzamidine, 15 a. N,N'-Bis(4-ethoxycarbonylphenyl)-4-nitrobenzamidine hydrochloride, 17

To a stirred suspension of ethyl 4-N-(4-nitrobenzoyl)-aminobenzoate (29.8 g; 0.10 mole) in dichloromethane (300 ml) was added phosphorus pentachloride (22.2 g; 0.11 mole) in small portions. The reaction mixture was allowed to reflux for 3 h; ethyl 4-aminobenzoate (16.5 g; 0.10 mole) was then added in small portions. The mixture was allowed to stir at reflux for 3 h and at room temperature overnight, then quenched with ice-water (300 ml) and neutralized with concentrated ammonium hydroxide. The organic layer was concentrated to an orange mass, which was triturated with hot toluene, filtered, and dried to yield the salt (34.4 g; 78.5%) as an off-white solid: mp 238°–242° C. $^1$H-NMR (DMSO-d$_6$) 8.4–7.0 (m, 14H), 4.2 (q, 4H, J=7 Hz), 1.3 (t, 6H, J=7 Hz); IR (Nujol) 1725, 1550; MS (m/e) 461 (M+-HCl), 36 (base).

b. N,N'-Bis(4-ethoxycarbonylphenyl)-4-nitrobenzamidine, 15

The salt prepared as in part a (1.0 g) was dissolved in warm methanol (20 ml) with vigorous stirring. The solution was brought to pH 8 by dropwise addition of pyridine, then was cooled and filtered. The resultant precipitate was washed with methanol and dried to yield the benzamidine (0.8 g; 87.0%) as yellow crystals: mp 202°–205° C. $^1$H-NMR (CDCl$_3$) 8.1–7.0 (m, 13H), 4.3 (q, 4H, J=7 Hz), 1.3 (t, 6H, J=7 Hz); IR (Nujol) 3300, 1710, 1680, 1590; MS (m/e) 461 (M+), 297 (base).

EXAMPLE 3

Scheme II: Preparation of N,N'-Bis(4-ethoxycarbonylphenyl)-2-methoxybenzamidine, 6

To a stirred solution of ethyl 4-N-(2-methoxybenzoyl)aminobenzoate (15.0 g; 0.05 mole) in dichloromethane (150 mL) was added phosphorus pentachloride (11.1 g; 0.053 mole) in small portions. After the addition was completed, the mixture was allowed to reflux for 1 h. Ethyl 4-aminobenzoate (8.3 g; 0.050 mole) was added in small portions and the solution was allowed to stir at reflux for 3 h, and at room temperature for 18 h. The reaction mixture was poured into ice-water (150 mL) and neutralized with concentrated ammonium hydroxide. The organic phase was concentrated to a yellow solid, which was triturated with wet diethyl ether with gentle warming to yield a white solid (28 g). Recrystallization from isopropanol gave the benzamidine (15.5 g; 68.9%.) as white crystals: mp 163°–164° C. $^1$H-NMR (CDCl$_3$) 7.9–6.6 (m, 13H), 4.2 (q, 4H, J=7 Hz), 3.6 (s, 3H), 1.3 (t, 6H, J=7 Hz); IR (Nujol) 3370, 1700, 1585; MS (m/e) 446 (M+) 282 (base).

EXAMPLE 4

Scheme II: Preparation of N-(4-Biphenyl)-N'-(4-ethoxycarbonylphenyl)benzamidine, 5

To a stirred solution of ethyl 4-(N-benzoyl)aminobenzoate 13.5 g; 0.05 mole) in chloroform (150 mL) was added phosphorus pentachloride (11.5 g; 0.055 mole) in small portions. The reaction mixture was allowed to reflux for 1 h, after which 4-aminobiphenyl (8.5 g; 0.05 mole) was added in small portions. The mixture was refluxed for 2 h, then poured into ice-water (150 mL) and neutralized with concentrated ammonium hydroxide. The organic phase was filtered and concentrated to a yellow solid. Recrystallization from toluene yielded the benzamidine 3.5 g; 16.7%) as pale-yellow crystals: mp 155°–158° C. $^1$H-NMR (CDCl$_3$) 8.0–6.8 (m, 19H), 4.2 (q, 2H, J=7 Hz), 1.3 (t, 3H, J=7 Hz); IR (CHCl$_3$) 3430, 1695, 1585; MS (m/e) 420 (M+), 252 (base).

EXAMPLE 5

Scheme II: Preparation of N,N'-Bis-(4-ethoxycarbonylphenyl)-4-methoxybenzamidine, 7

Phosphorus oxychloride (76.8 g, 0.5 mol) was added dropwise to a stirred solution of 4-methoxybenzoic acid (40 g, 0.26 mol), benzocaine (82.4 g, 0.5 mol) and toluene (500 ml) at 80° C. The reaction was refluxed for 24 hrs. then quenched with 30% sodium hydroxide. The organic phase was then separated, cooled and the resulting precipitate recrystallized from toluene to yield the benzamidine (48 g, 43%) as a pale yellow solid: mp 145°–146° C. H-NMR (CDCl$_3$) 1.36 (t, 6H), 3.78 (s, 3H), 4.29–4.37 (Q, 4H), 6.7–8.0 (m, 13H); IR (CHCl$_3$) 1710, 1690, 1640, 1605, 1590, 1260; MS (m/e) 426 (m+) 282 (base).

EXAMPLE 6

Preparation of additional N,N'-diarylbenzamidines reported in Table I.

a. N,N'-Bis(4-methoxycarbonylphenyl)benzamidine (1) was prepared from methyl 4-aminobenzoate and α,α,α-trichlorotoluene; pale-yellow crystals: mp 180°–182° C. $^1$H-NMR (CDCl$_3$) 8.0–7.0 (m, 14H), 3.8 (s, 6H); IR (CDCl$_3$) 3330, 1705, 1585; MS (m/e) 388 (M+), 238 (base).

b. N,N'-Bis[4-(2-ethylhexyl)oxycarbonylphenyl]benzamidine (3) was prepared from 2-ethylhexyl 4-aminobenzoate and α,α,α-trichlorotoluene; viscous, gold oil: $^1$H-NMR (CDCl$_3$) 7.9–6.8 (m, 14H), 4.1 (d, 4H, J=4 Hz), 1.9–0.8 (m, 30H); IR (Neat) 3330, 1710, 1585; MS (m/e) 584 (M+), 336 (base).

c. N,N'-Bis(4-n-octylcarbamylphenyl)benzamidine (4) was prepared from 4-amino-N-n-octylbenzamide and α,α,α-trichlorotoluene; pale-yellow oil: $^1$H-NMR (CDCl$_3$) 7.7–6.9 (m, 14H), 6.2 (br t, 2H, J=6 Hz), 3.3 (br q, 4H, J=6 Hz), 1.7–0.7 (m, 30H); IR (CHCl$_3$) 3430, 1640, 1590; MS (m/e) 582 (M+), 335 (base).

d. N,N'-Bis(4-ethoxycarbonylphenyl)-4-cyanobenzamidine (8) was prepared from ethyl 4-[N-(4-cyanobenzoyl)]-aminobenzoate, phosphorus pentachloride, and ethyl 4-aminobenzoate; pale-yellow crystals: mp 205°–213° C. $^1$H-NMR (DMSO-d$_6$), 8.1–7.4 (m, 13H), 4.2 (q, 4H, J=7 Hz), 1.3 (t, 6H, J=7 Hz); IR (CHCl₃) 3320, 1705, 1590; MS (m/e) 441 (M+), 277 (base).

e. N,N'-Bis(4-ethoxycarbonylphenyl)-4-phenylbenzamidine (9) was prepared from ethyl 4-[N-(4-phenylbenzoyl)]-aminobenzoate, phosphorus oxychloride, and ethyl 4-aminobenzoate; pale-yellow solid: mp 152°-160° C. ¹H-NMR (CDCl₃) 8.0–6.9 (m, 18H), 4.2 (q, 4H, J=7 Hz), 1.3 (t, 6H, J=7 Hz); IR (CHCl₃) 3420, 1700, 1590; MS (m/e) 492 (M+), 328 (base).

f. N,N'-Bis(4-ethoxycarbonylphenyl)-2-chlorobenzamidine (10) was prepared from ethyl 4-aminobenzoate and α,α,α,2-tetrachlorotoluene; tan solid: mp 98°-108° C. ¹H-NMR (CDCl₃) 8.3–6.4 (m, 13H), 4.2 (q, 4H, J=7 Hz); IR (CHCl₃) 3360, 1695, 1600, 1580; MS (m/e) 450, 452 (M+), 286 (base).

g. N,N'-Bis(4-ethoxycarbonylphenyl)-3-chlorobenzamidine (11) was prepared from ethyl 4-[N-(3-chlorobenzoyl)] aminobenzoate, phosphorus pentachloride, and ethyl 4-aminobenzoate; yellow crystals: mp 160°-170° C. ¹H-NMR (CDCl₃) 8.0–6.8 (m, 13H), 4.2 (q, 4H, J=7 Hz), 1.3 (t, 6H, J=7 Hz); IR (CDCl₃) 3330, 1705, 1590; MS (m/e) 450, 452 (M+), 286 (base).

h. N,N'-Bis(4-ethoxycarbonylphenyl)-4-chlorobenzamidine (12) was prepared from ethyl 4-[N-(4-chlorobenzoyl)] aminobenzoate, phosphorus pentachloride, and ethyl 4-aminobenzoate; white crystals: mp 171.0°-172.5° C. ¹H-NMR (CDCl₃) 8.0–6.9 (m, 13H), 4.2 (q, 4H, J=7 Hz), 1.5 (t, 6H, J=7 Hz); IR (CHCl₃) 3420, 3330, 1705, 1590; MS (m/e) 450, 452 (M+), 286 (base).

i. N,N'-Bis(4-ethoxycarbonylphenyl)-4-methylbenzamidine (13) was prepared from ethyl 4-[N-(4-toluyl)] aminobenzoate, phosphorus oxychloride, and ethyl 4-aminobenzoate; pale-yellow solid: mp 246°-260° C. ¹H-NMR (CDCl₃) 8.1–6.3 (m, 13H), 4.3 (q, 4H, J=7 Hz), 2.3 (s, 3H), 1.3 (t, 6H, J=7 Hz); IR (CHCl₃) 3420, 1710, 1590; MS (m/e) 430 (M+), 266 (base).

j. N,N'-Bis(4-ethoxycarbonylphenyl)-4-t-butylbenzamidine (14) was prepared from ethyl 4-[N-(4-t-butylbenzoyl)]aminobenzoate, phosphorus pentachloride, and ethyl 4-aminobenzoate; yellow solid: mp 212°-219° C. ¹H-NMR (CDCl₃) 8.0–7.0 (m, 12H), 6.0 (br s, 1H), 4.3 (q, 4H, J=7 Hz), 1.4 (t, 6H, J=7 Hz), 1.3 (s, 9H); IR (Nujol) 3330, 1710, 1590; MS (m/e) 472 (M+), 308 (base).

We claim:

1. A compound of the formula

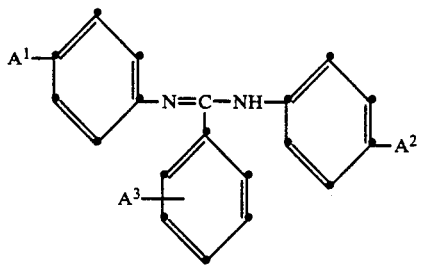

I wherein:

A¹ and A² may be the same or different and represent —COOR¹, —CONR¹R², —C≡N or —C₆H₅;

A³ represents —H, —OH, —OR, —Cl, —NO₂, —C≡N, —C₆H₅, or an alkyl group of one to five carbon atoms;

R¹ and R² may be the same or different and represent hydrogen or an alkyl group of one to ten carbon atoms; and, R represents an alkyl group of one to ten carbon atoms.

2. A compound according to claim 1 wherein R¹ and R² are methyl or ethyl.

3. A compound according to claim 1 wherein A¹ and A² are both —COOR¹.

4. A compound according to claim 3 wherein A³ is hydrogen or —OR.

5. A compound according to claim 4 wherein R¹ is methyl or ethyl.

6. A compound according to claim 5 wherein A³ is hydrogen or methoxy.

7. The compound according to claim 6 wherein R¹ is ethyl and A³ is hydrogen.

8. A compound according to claim 6 wherein R¹ is ethyl and A³ is methoxy.

9. The compound according to claim 8 which is N,N'-bis-(4-ethoxycarbonylphenyl)-2-methoxybenzamidine.

10. The compound according to claim 8 which is N,N'-bis-(4-ethoxycarbonylphenyl)-4-methoxybenzamidine.

11. An ultraviolet-absorbing composition comprising a compound of the formula

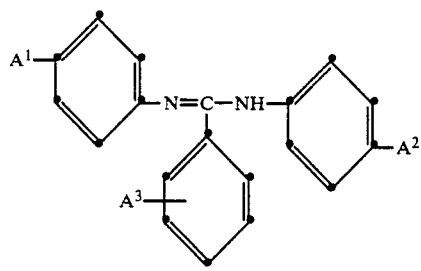

I wherein:

A¹ and A² may be the same or different and represent —COOR¹, —CONR¹R², —C≡N or —C₆H₅;

A³ represents —H, —OH, —OR, —Cl, —NO₂, —C≡N, —C₆H₅, or an alkyl group of one to five carbon atoms;

R¹ and R² may be the same or different and represent hydrogen or an alkyl group of one to ten carbon atoms; and, R represents an alkyl group of one to ten carbon atoms, and at least one organic material subject to degradation by ultraviolet light.

12. A composition according to claim 11 wherein R¹ and R² are methyl or ethyl.

13. A composition according to claim 11 wherein A¹ and A² are both —COOR¹.

14. A composition according to claim 13 wherein A³ is hydrogen or —OR.

15. A composition according to claim 14 wherein R¹ is methyl or ethyl.

16. A composition according to claim 15 wherein A³ is hydrogen or methoxy.

17. The composition according to claim 16 wherein R¹ is ethyl and A³ is hydrogen.

18. A composition according to claim 16 wherein R¹ is ethyl and A³ is methoxy.

19. The composition according to claim 18 wherein the compound is N,N'-bis(4-ethoxycarbonylphenyl)-2-methoxybenzamidine.

20. The composition according to claim 18 wherein the compound is N,N'-bis(4-ethoxycarbonylphenyl)-4-methoxybenzamidine.

* * * * *